(12) United States Patent
Sugimoto (10) Patent No.: US 10,828,024 B2
(45) Date of Patent: Nov. 10, 2020

(54) LIGATION DEVICE

(71) Applicant: OLYMPUS CORPORATION, Tokyo (JP)

(72) Inventor: Naoya Sugimoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 220 days.

(21) Appl. No.: 15/918,084

(22) Filed: Mar. 12, 2018

(65) Prior Publication Data

US 2018/0199935 A1    Jul. 19, 2018

Related U.S. Application Data

(63) Continuation of application No. PCT/JP2015/083417, filed on Nov. 27, 2015.

(51) Int. Cl.
*A61B 17/04* (2006.01)
*A61B 17/12* (2006.01)
(Continued)

(52) U.S. Cl.
CPC .... *A61B 17/0491* (2013.01); *A61B 17/06066* (2013.01); *A61B 17/12013* (2013.01);
(Continued)

(58) Field of Classification Search
USPC ....... 606/113, 139, 144, 145, 146, 147, 148, 606/232
See application file for complete search history.

(56) References Cited

U.S. PATENT DOCUMENTS

| 6,679,892 B2 * | 1/2004 | Guido | A61B 17/12013 606/113 |
| 2003/0065335 A1 * | 4/2003 | Guido | A61B 17/12013 606/144 |

(Continued)

FOREIGN PATENT DOCUMENTS

| JP | 2007-534355 A | 11/2007 |
| JP | 2012-522596 A | 9/2012 |

(Continued)

OTHER PUBLICATIONS

International Search Report dated Jan. 26, 2016 issued in PCT/JP2015/083417.

*Primary Examiner* — Kathleen S Holwerda
*Assistant Examiner* — Kankindi Rwego
(74) *Attorney, Agent, or Firm* — Scully, Scott, Murphy & Presser, P.C.

(57) ABSTRACT

According to an embodiment of the present invention, there is provided a ligation device that includes an insertion portion that has a lumen through which are passed a ligature having a first end having a contractible loop formed by a knot, and a pull thread having a folded-back portion fed through the loop; an operation portion provided at a proximal end portion of the insertion portion, the operation portion including a anchoring portion to which a first end of the pull thread is anchored; and a movable member movable relative to the operation portion while switching between a first state in which a second end of the pull thread is anchored to the movable member and pulled and a second state in which the ligature is pulled and the pull thread is let out simultaneously.

6 Claims, 9 Drawing Sheets

(51) Int. Cl.
   *A61B 17/06* (2006.01)
   *A61B 17/00* (2006.01)
(52) U.S. Cl.
   CPC ............... *A61B 2017/00243* (2013.01); *A61B 2017/00358* (2013.01); *A61B 2017/00367* (2013.01); *A61B 2017/0496* (2013.01); *A61B 2017/061* (2013.01)

(56) References Cited

U.S. PATENT DOCUMENTS

| | | |
|---|---|---|
| 2005/0154404 A1 | 7/2005 | Liddicoat et al. |
| 2007/0073313 A1 | 3/2007 | Liddicoat et al. |
| 2008/0147097 A1 | 6/2008 | Liddicoat et al. |
| 2008/0221593 A1 | 9/2008 | Liddicoat et al. |
| 2010/0094316 A1 | 4/2010 | Rupp et al. |
| 2011/0087247 A1 | 4/2011 | Fung et al. |
| 2016/0120549 A1 | 5/2016 | Fung et al. |
| 2016/0235412 A1 | 8/2016 | Liddicoat et al. |
| 2017/0290591 A1 | 10/2017 | Liddicoat et al. |

FOREIGN PATENT DOCUMENTS

| | | |
|---|---|---|
| WO | WO 2005/034802 A2 | 4/2005 |
| WO | WO 2008/071367 A1 | 6/2008 |
| WO | WO 2010/115030 A1 | 10/2010 |

\* cited by examiner

LIGATION DEVICE

CROSS-REFERENCE TO RELATED APPLICATIONS

This is a continuation of International Application PCT/JP2015/083417, with an international filing date of Nov. 27, 2015, which is hereby incorporated by reference herein in its entirety.

TECHNICAL FIELD

The present invention relates to a ligation device.

BACKGROUND ART

A ligation device equipped with a snare loop assembly constituted by a snare and a ligature loop prepared by forming a loop with a ligature is known and is used to ligate tissue (for example, refer to PTL 1).

In this ligation device, the snare loop assembly can be opened and closed by operating the snare. After the snare loop assembly is put in a close state to temporarily tighten the tissue and the state of ligation is checked, the tissue is fully tightened by using the ligature loop while the same state is maintained.

CITATION LIST

Patent Literature

{PTL 1} Japanese Translation of PCT International Application, Publication No. 2012-522596

SUMMARY OF INVENTION

Technical Problem

An object of the present invention is to provide a ligation device that can perform temporary tightening and full tightening by using a ligature loop without using a snare.

Solution to Problem

According to an embodiment of the present invention, there is provided a ligation device that includes an insertion portion that has a lumen through which are passed a ligature having a first end having a contractible loop formed by a knot, and a pull thread having a folded-back portion fed through the loop; an operation portion disposed on a proximal-end side of the insertion portion, the operation portion including a anchoring portion to which a first end of the pull thread is anchored; and a movable member movable relative to the operation portion while switching between a first state in which a second end of the pull thread is anchored to the movable member and pulled and a second state in which the ligature is pulled and the pull thread is let out simultaneously.

In the aspect described above, in the first state, the ligature may be attached to the operation portion and the second end of the pull thread may be pulled, and in the second state, the ligature may be attached to the movable member, and the ligature is pulled and the pull thread may be let out simultaneously.

In the aspect described above, the ligation device may also include a first attaching portion to which a second end of the ligature is to be attached, the first attaching portion provided in the operation portion; and a second attaching portion to which the second end of the ligature extending to the outside from a proximal end of the lumen is to be attached, the second attaching portion provided in the movable member. When the movable member is in the first state, the second end of the ligature may be attached to the first attaching portion, and in the second state, the second end of the ligature may be attached to the second attaching portion.

In the aspect described above, the movable member may switched between the first state in which the second end of the pull thread is pulled by a predetermined length, and a second state in which the ligature is pulled and the pull thread is let out by the predetermined length simultaneously.

In the aspect described above, when the movable member is in the first state, the movable member may be moved relative to the operation portion so that the pull thread is pulled, and the second end of the ligature may be detachably anchored to the movable member at a position where a part of the loop is withdrawn into the lumen.

In the aspect described above, when the movable member is in the first state, the pull thread may be pulled, and the second end of the ligature may be detachably anchored to the movable member at a position where the folded-back portion of the pull thread is withdrawn by a length equal to one half of the predetermined length.

In the aspect described above, the ligation device may further include a pulley that is provided in the operation portion and folds back the ligature, and the movable member may be a slider linearly movable in the longitudinal direction of the pull thread, and the ligature folded back by the pulley may be to be detached from or attached to the slider.

In the aspect described above, the movable member may be a spool member rotatable about an axial line extending in a direction orthogonal to the longitudinal direction of the pull thread, and the second end of the ligature may be attached to the movable member so that a winding direction of the ligature is opposite to a winding direction of the pull thread.

In the aspect described above, when the movable member is in the first state, the ligature may be pulled in a proximal end direction, and the second end of the pull thread in a state in which a part of the loop is withdrawn into the lumen may be detachably anchored to the movable member.

In the aspect described above, the ligature may be pulled in the proximal end direction, and the second end of the pull thread in a state in which the folded-back portion of the pull thread may be withdrawn by one half of the predetermined length is detachably anchored to the movable member.

In the aspect described above, the ligation device may further include a pulley that folds back the pull thread, the pulley being provided in the operation portion, the movable member may be a slider linearly movable in the longitudinal direction of the ligature, and the pull thread folded back by the pulley may be detachably attached to the slider.

In the aspect described above, the movable member may be a spool member rotatable about an axial line extending in a direction orthogonal to the longitudinal direction of the ligature, and the second end of the pull thread may be attached to the movable member so that a winding direction of the pull thread is opposite to a winding direction of the ligature.

In the aspect described above, the insertion portion may have a plurality of the lumens, and the ligature and the pull thread may be disposed in different lumens.

In the aspect described above, the insertion portion may have one lumen, and a knot receiving portion that has a penetrating hole having a diameter larger than a line diameter of the ligature and smaller than the knot may be installed at a distal end of the insertion portion.

In the aspect described above, when the movable member is in the first state, the second end may be pulled in a first direction, and in the second state, the ligature is pulled and the pull thread may be let out simultaneously in a second direction opposite to the first direction.

DESCRIPTION OF EMBODIMENTS

A ligation device 1 according to an embodiment of the present invention will now be described with reference to the drawings.

Figure 1:
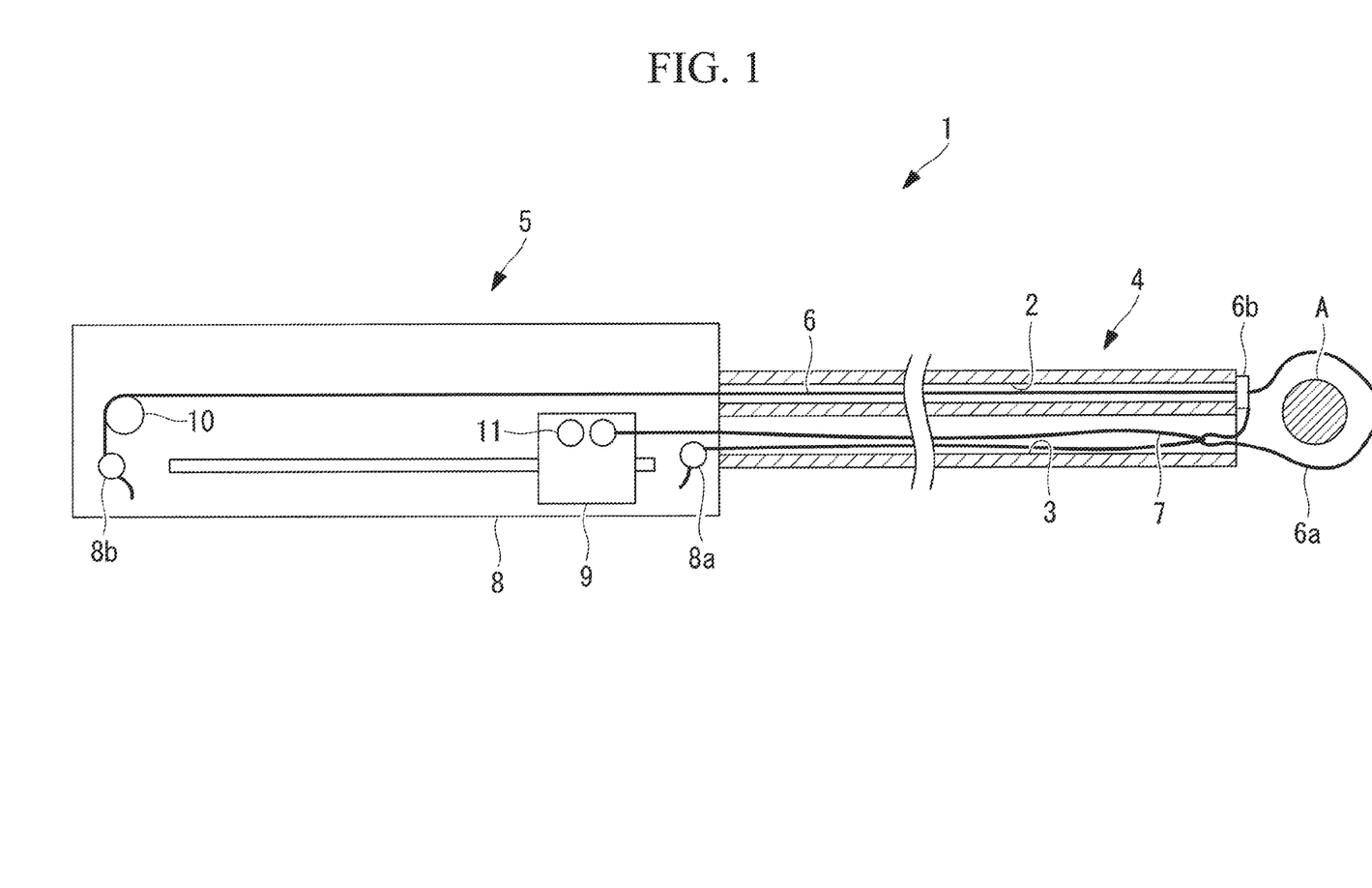
FIG. 1 is a longitudinal sectional view of a ligation device according to one embodiment of the present invention.

The ligation device 1 according to this embodiment is a device that ligates the left atrial appendage A, and, as illustrated in FIG. 1, is equipped with a thin long insertion portion 4 having two lumens 2 and 3 passing through the insertion portion 4 in the longitudinal direction; an operation portion 5 disposed on a proximal-end side of the insertion portion 4; a ligature 6 disposed inside the lumen 2 in the insertion portion 4; and a pull thread 7 disposed inside the lumen 3.

The insertion portion 4 has a length sufficient to bring a distal end thereof to the vicinity of the left atrial appendage A in the pericardial space via a sheath arranged to penetrate from the lower portion of the ensiform cartilage to the interior of the pericardial space.

The ligature 6 has a loop 6a, which is formed by a knot 6b, at one end (first end). The knot 6b has a size larger than the opening of the lumen 2 at the distal end of the insertion portion 4 and a size sufficient to prevent withdrawal into the lumen 2. The other end (second end) of the ligature 6 extends to the outside from the proximal end of the insertion portion 4 via the lumen 2. When the second end of the ligature 6 is pulled at the proximal end of the insertion portion 4, the knot 6b stays at the distal end of the insertion portion 4 and causes the loop 6a to contract.

The pull thread 7 is disposed inside the lumen 3 such that the pull thread 7 is folded back at a middle position in the longitudinal direction, and both ends of the pull thread 7 extend to the outside from the opening at the proximal end of the insertion portion 4. One end (first end) of the pull thread 7 is, for example, anchored to an anchoring portion 8a of a housing 8 of the operation portion 5, so as to be anchored relative to the insertion portion 4; and the other end (second end) can be pulled.

The loop 6a of the ligature 6 is fed through the folded-back portion of the pull thread 7. In this manner, when the second end of the pull thread 7 is pulled toward the proximal-end side, the loop 6a of the ligature 6 is partly withdrawn into the lumen 3, and the length of the loop 6a exposed on the outer side of the distal end of the insertion portion 4 is decreased.

The operation portion 5 is equipped with the housing 8 fixed to the proximal end of the insertion portion 4; a slider (movable member) 9 linearly movable in the longitudinal direction of the insertion portion 4 relative to the housing 8; and a pulley 10 supported on the housing 8 to be rotatable about the axial line orthogonal to the longitudinal direction of the insertion portion 4. The second end of the pull thread 7 extending to the outside from the proximal end opening of the lumen 3 of the insertion portion 4 is anchored to the slider 9. The slider 9 has an attaching portion (second attaching portion) 11 to which the second end of the ligature 6 is detachably attached. In the drawing, reference numeral 8b denotes an attaching portion (first attaching portion) to which the second end of the ligature 6 is temporarily attached.

The ligature 6 extending to the outside from the proximal end opening of the lumen 2 is put around the pulley 10. The second end of the ligature 6, which has been folded back by being put around the pulley 10, is detachable from the attaching portion 8b and attachable to the attaching portion 11 of the slider 9.

The operation of the ligation device 1 of this embodiment having the above-described structure will now be described.

In order to ligate the left atrial appendage A by using the ligation device 1 of this embodiment, the distal end of the insertion portion 4 is extended to the vicinity of the left atrial appendage A in the pericardial space through a sheath (not illustrated in the drawings), and the distal end of the insertion portion 4 is advanced under observation with an endoscope (not illustrated in the drawings) separately inserted into the pericardial space. Then, the left atrial appendage A is inserted into the loop 6a until the loop 6a of the ligature 6 exposed at the distal end of the insertion portion 4 reaches the position at which the loop 6a can be placed around the base of the left atrial appendage A.

During this process, as illustrated in FIG. 1, the slider 9 of the operation portion 5 is sufficiently advanced so that the length of the loop 6a exposed at the distal end of the insertion portion 4 is substantially the maximum. In this manner, the left atrial appendage A can be smoothly inserted into the big loop 6a.

Figure 2:
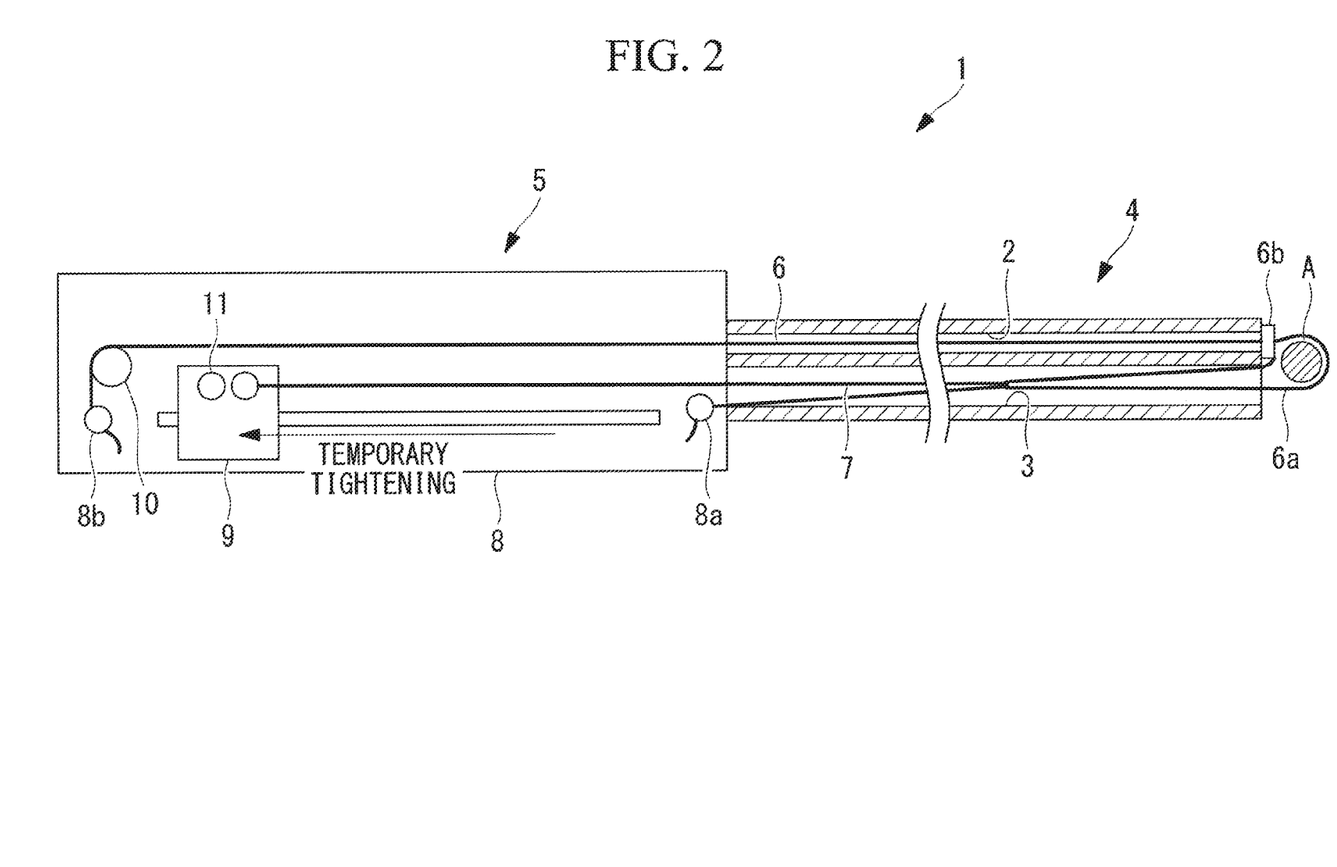
FIG. 2 is a longitudinal sectional view illustrating temporary tightening performed by the ligation device illustrated in FIG. 1.

While the loop 6a is disposed at a particular position at the base of the left atrial appendage A, as illustrated in FIG. 2, the user retracts (moves in the first direction) the slider 9 to pull the second end of the pull thread 7 attached to the slider 9 toward the proximal end (first state). Since the first end of the pull thread 7 is anchored to the anchoring portion 8a of the housing 8, pulling the second end moves the folded-back portion of the pull thread 7 inside the lumen 3 toward the proximal end.

Since the loop 6a of the ligature 6 is fed through the folded-back portion of the pull thread 7, the amount of the loop 6a of the ligature 6 withdrawn into the lumen 3 increases as the folded-back portion is moved. As a result, the length of the loop 6a exposed at the distal end of the insertion portion 4 is decreased, and the left atrial appendage A inserted in the loop 6a is tightened (temporary tightening).

At this point, the user can check, through an endoscopic image, whether or not the position at which the left atrial appendage A is tightened by the ligature 6 is appropriate. If, as a result of the check, it is found that the position is inappropriate, the slider 9 is advanced (moved in a second direction) to relax the pulling force applied to the pull thread 7 (second state).

Since the length of the loop 6a exposed at the distal end of the insertion portion 4 has been decreased by withdrawal of a part of the loop 6a into the lumen 3, the loop 6a itself remains uncontracted. Thus, by relaxing the pulling force of the pull thread 7, the loop 6a, which has been withdrawn in the lumen 3, can be pulled out of the lumen 3, the left atrial appendage A can be untightened, and thus the tightening position etc., can be re-adjusted.

Figure 3:
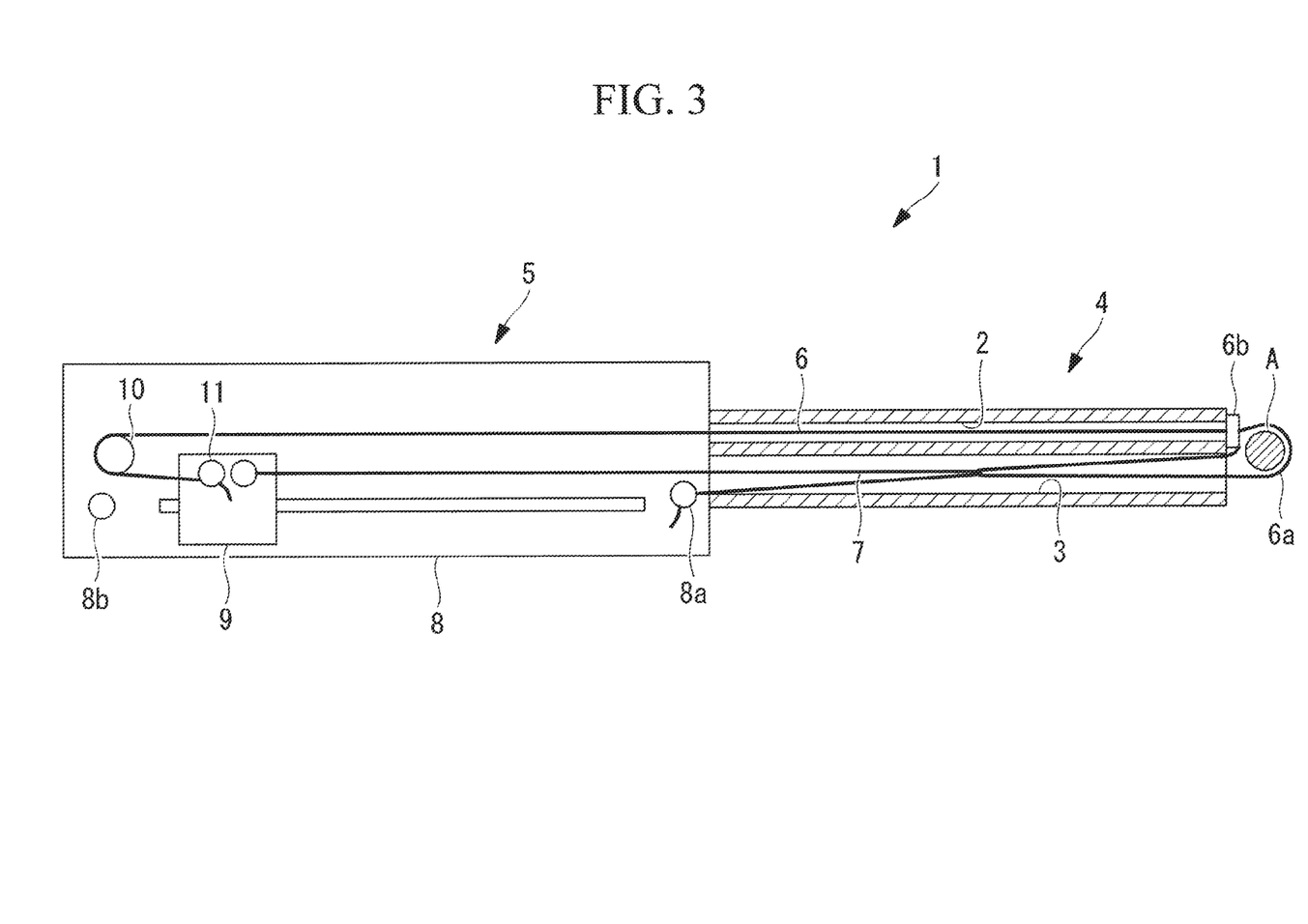
FIG. 3 is a longitudinal sectional view illustrating a step of preparing full tightening performed by the ligation device illustrated in FIG. 1.

If, as a result of the check, it is found that the position at which the ligature 6 tightens the left atrial appendage A is appropriate, as illustrated in FIG. 3, the second end of the ligature 6 detached from the attaching portion 8b of the housing 8 is anchored to the attaching portion 11 of the slider 9. During this process, the ligature 6 is preferably anchored with as little slack as possible.

Figure 4:
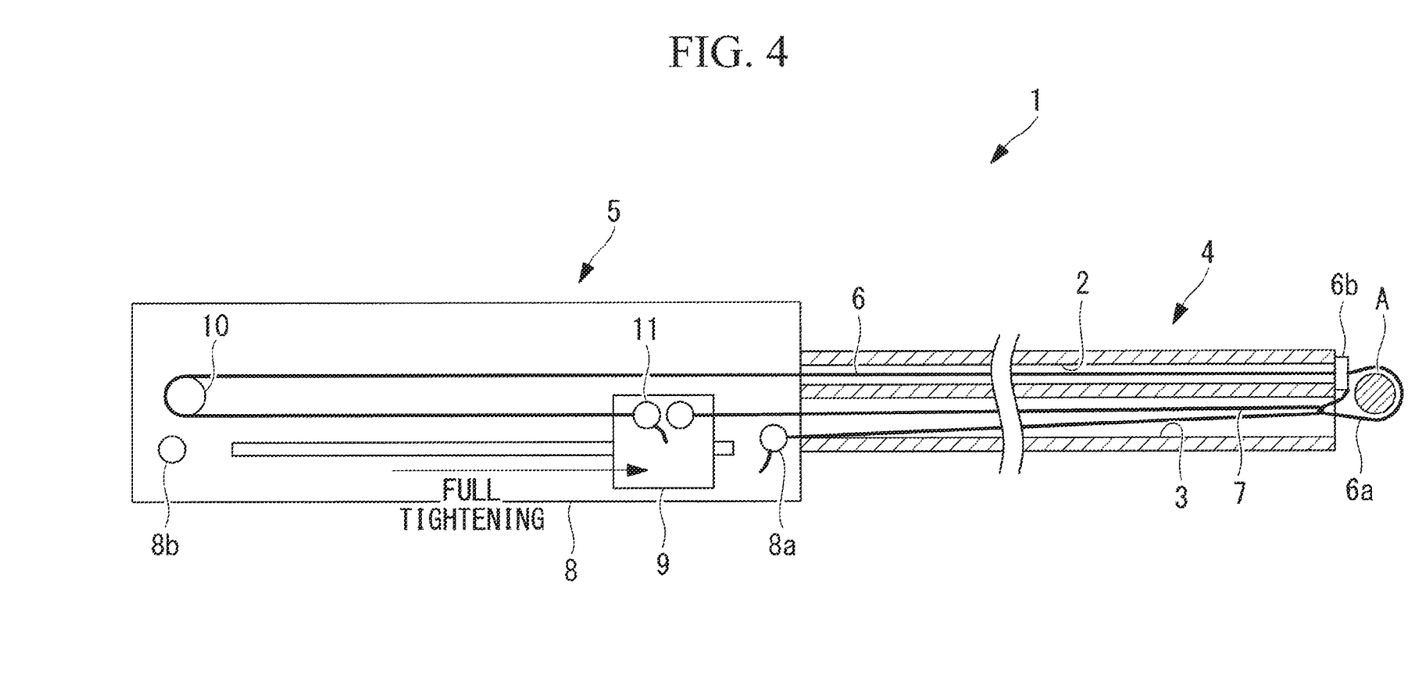
FIG. 4 is a longitudinal sectional view illustrating full tightening performed by the ligation device illustrated in FIG. 1.

While maintaining this state, as illustrated in FIG. 4, the slider 9 is operated to advance so that pulling force acts on the ligature 6 folded back by the pulley 10 and anchored to the slider 9 and so that the second end of the pull thread 7, to which pulling force has been applied, moves in a direction in which the pulling force is relaxed. Since the ligature 6 and the pull thread 7 are anchored to the same slider 9, the amount of movement of the ligature 6 and the amount of movement of the pull thread 7 can be made equal to each other.

When the ligature 6 is pulled, the ligature 6 moves relative to the knot 6b hung at the distal end of the insertion portion 4. As a result, the loop 6a is contracted, and the pull thread 7 is let out so that the folded-back portion advances inside the lumen 3. During this process, since the amount of movement is the same between the ligature 6 and the pull thread 7, the pull thread 7 moves by the same amount as the amount of movement of the ligature 6 that causes the loop 6a to contract, and thus a portion of the loop 6a that has been withdrawn in the lumen 3 is pulled out of the lumen 3. Here, the diameter of the loop 6a remains constant.

This is because the loop 6a is pulled out of the insertion portion 4 by an amount A of movement of the slider 9. The loop 6a is folded back by the pull thread 7 in the insertion portion 4, and thus, the amount of movement of the position of the folded-back portion of the loop 6a in the longitudinal direction of the insertion portion 4 is A/2. Accordingly, the position of the folded-back portion of the pull thread 7 also moves by A/2. Since the first end of the pull thread 7 is anchored to the operation portion, the second end of the pull thread 7 is pulled by a length A. Thus, because the operation is performed while the ligature 6 and the pull thread 7 are anchored to the same slider 9, the diameter of the loop 6a remains constant.

The portion of the loop 6a that has been withdrawn in the lumen 3 becomes entirely exposed on the outer side of the lumen 3, and thus, full tightening of the left atrial appendage A by the loop 6a of the ligature 6 can be performed. In other words, according to this embodiment, the temporary tightening state of the left atrial appendage A by the ligature 6 can be smoothly transitioned to the full tightening state of the left atrial appendage A by the ligature 6. Thus, an advantage is offered in that the ligation by full tightening can be performed without shifting the ligation position determined by temporary tightening.

After completion of the full tightening by the loop 6a of the ligature 6, forceps (not illustrated in the drawings) separately introduced into the pericardial space cut the ligature 6 on the proximal end side of the knot 6b. When the pull thread 7 exposed outside the body from the proximal end of the insertion portion 4 is removed from the slider 9 or cut, the pull thread 7 fed through the loop 6a of the ligature 6 can be removed from the ligature 6.

As described above, the ligation device 1 of this embodiment offers advantages in that temporary tightening and full tightening by the loop 6a of the ligature 6 can be performed without using a snare and that the diameter of the insertion portion 4 can be reduced due to the simple structure.

Figure 5:
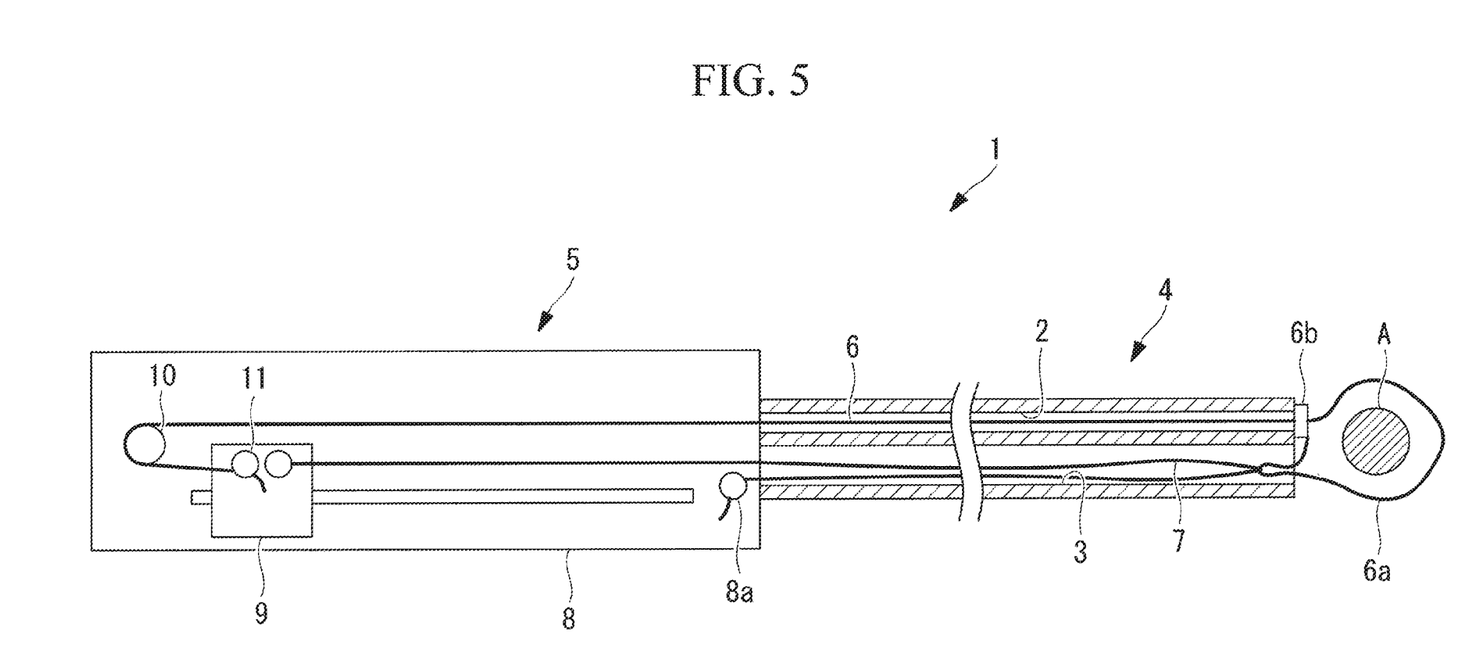
FIG. 5 is a longitudinal sectional view of a first modification of the ligation device illustrated in FIG. 1.

In the ligation device 1 of this embodiment, the pull thread 7 is attached to the slider 9, which can be moved relative to the housing 8, in advance; while temporary tightening is performed by moving the slider 9 in one direction, the second end of the ligature 6 is anchored to the slider 9; and the slider 9 is moved in the opposite direction to perform full tightening. However, the invention is not limited thereto. In other words, as illustrated in FIG. 5, regarding the connecting state with respect to the slider 9, the pull thread 7 and the ligature 6 may be interchanged. That is, the second end of the ligature 6 may be attached to the slider 9 in advance; and while temporary tightening is performed by the user by pulling the second end of the pull thread 7 with his/her hand or by using another slider (not illustrated), the second end of the pull thread 7 may be anchored to the slider 9 or another slider may be joined to the slider 9 so as to perform full tightening by moving the slider 9.

Figure 6:
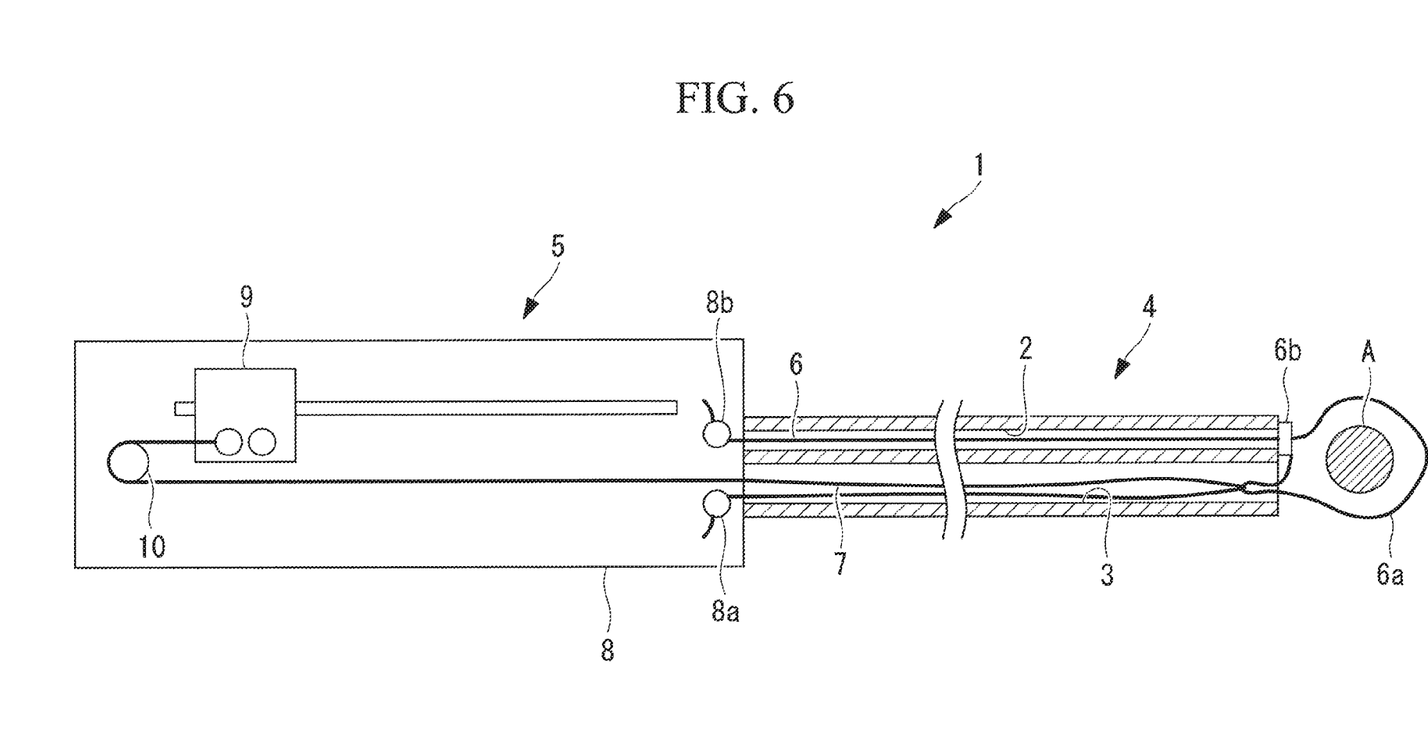
FIG. 6 is a longitudinal sectional view of a second modification of the ligation device illustrated in FIG. 1.

The ligature 6 is folded back by the pulley 10 and anchored to the slider 9; alternatively, the pull thread 7 folded back by the pulley 10 may be anchored to the slider 9 in advance, as illustrated in FIG. 6. In order to fold back the ligature 6, not only a structure that rotates like a wheel, such as the pulley 10, but also a structure that merely changes the direction in which the ligature 6 runs and that is anchored to the operation portion 5 may be used.

Figure 7:
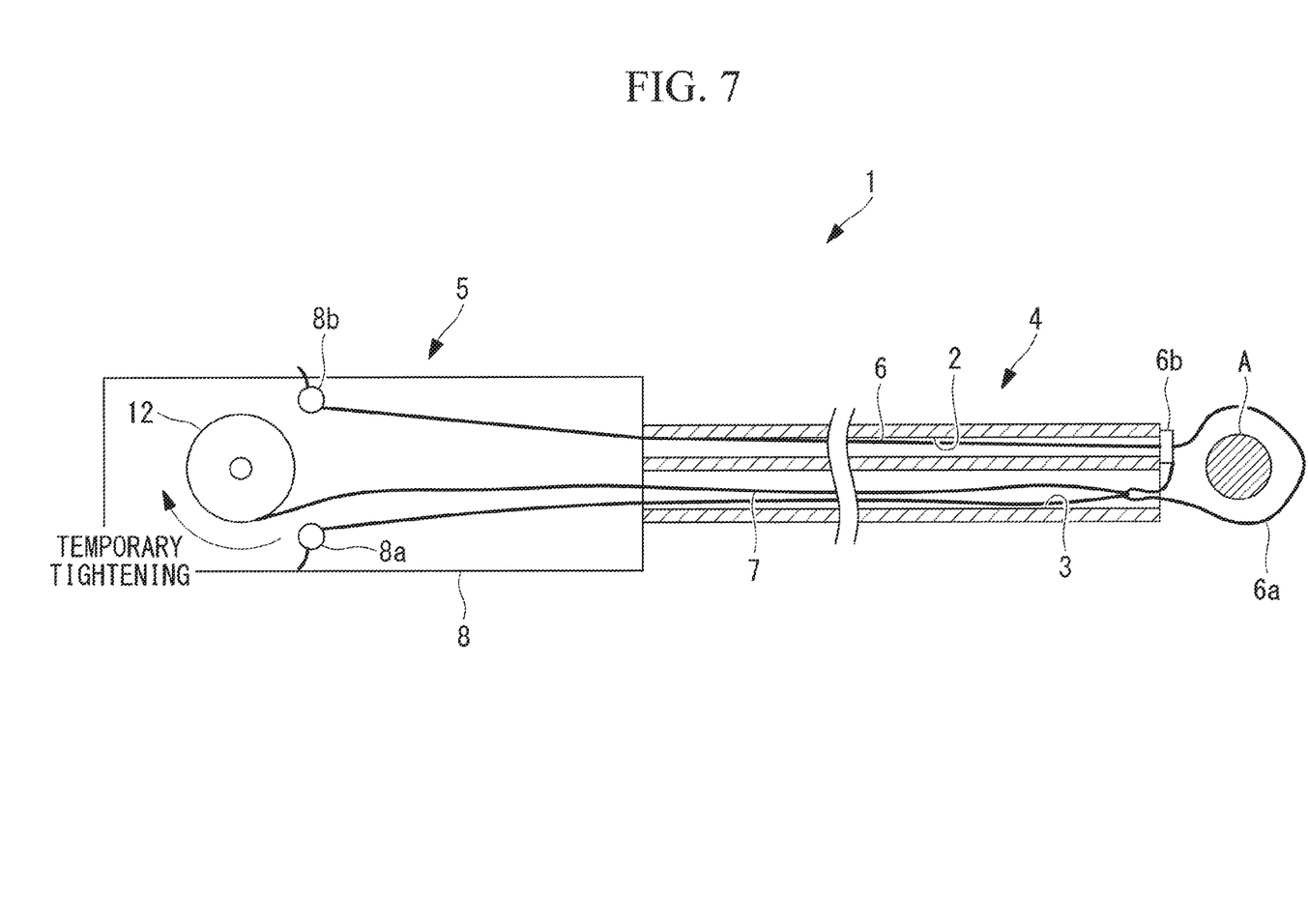
FIG. 7 is a longitudinal sectional view of a third modification of the ligation device illustrated in FIG. 1.

In this embodiment, the slider 9 is described as an example of the movable member. Alternatively, as illustrated in FIG. 7, a spool member 12 on which the ligature 6 and the pull thread 7 are wound may be employed.

The spool member 12 is, for example, a columnar member supported on the housing 8 so as to be rotatable about the axial line extending in a direction orthogonal to the longitudinal direction of the insertion portion 4. The second end of the pull thread 7 is anchored to the spool member 12 in advance, and, as illustrated by the arrow in FIG. 7, the spool member 12 is rotated in one direction so that a pulling force acts on the pull thread 7 and temporary tightening is performed.

Figure 8:
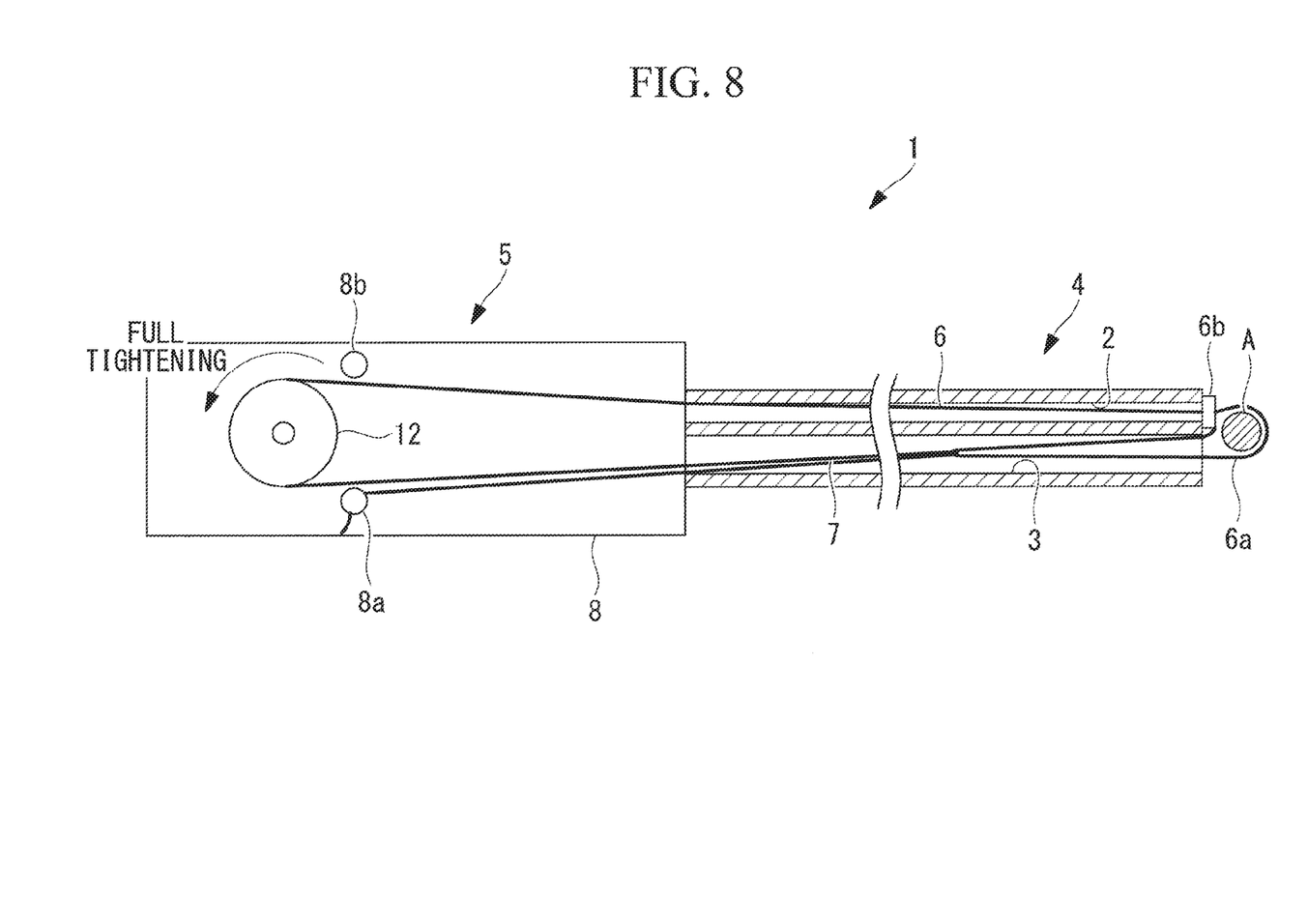
FIG. 8 is a longitudinal sectional view illustrating full tightening performed by the ligation device illustrated in FIG. 7.

In the temporary tightening state, as illustrated in FIG. 8, the second end of the ligature 6 is anchored to the spool member 12, and the spool member 12 is rotated in the opposite direction so that the ligature 6 can be pulled and the pull thread 7 can be let out simultaneously. In this manner, as with the slider 9, it is possible to switch between temporary tightening and full tightening, and an even simpler ligation device 1 can be configured since the pulley 10 that folds back the ligature 6 or the pull thread 7 is no longer necessary.

Figure 9:
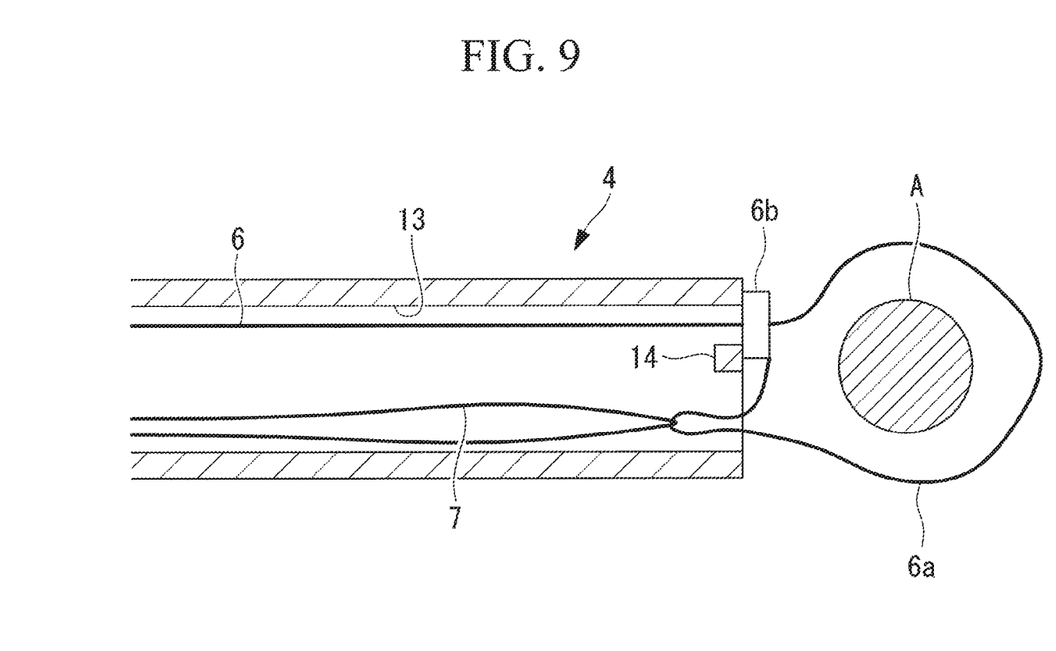
FIG. 9 is a partial longitudinal sectional view of a fourth modification of the ligation device illustrated in FIG. 1.

In this embodiment, the ligature 6 and the pull thread 7 that are moved at timings or directions different from each other are inserted into separate lumens 2 and 3; thus, interference is reduced, and smooth operation can be achieved. Alternatively, as illustrated in FIG. 9, an insertion portion having a single lumen 13 may be employed as the insertion portion 4, and a knot receiving portion 14 that prevents withdrawal of the knot 6*b* into the lumen 13 may be installed at the distal end of the insertion portion 4. In this manner, the structure of the insertion portion 4 can be simplified, and the diameter of the insertion portion 4 can be further reduced.

In this embodiment, the first end of the pull thread 7 is anchored to the housing 8 of the operation portion 5 so as to anchor the pull thread 7 with respect to the insertion portion 4; alternatively, the first end of the pull thread 7 may be anchored to the insertion portion 4 itself.

As a result, the following aspect is derived from the above-described embodiment.

According to an embodiment of the present invention, there is provided a ligation device that includes an insertion portion that has a lumen through which are passed a ligature having a first end having a contractible loop formed by a knot, and a pull thread having a folded-back portion fed through the loop; an operation portion disposed on a proximal-end side of the insertion portion, the operation portion including a anchoring portion to which a first end of the pull thread is anchored; and a movable member movable relative to the operation portion while switching between a first state in which a second end of the pull thread is anchored to the movable member and pulled and a second state in which the ligature is pulled and the pull thread is let out simultaneously.

According to this aspect, the ligature loop disposed on the outer side of the distal end of the insertion portion is put around the object to be ligated, and, in the first state and on the proximal end side of the insertion portion, the movable member is moved relative to the operation portion so as to pull the pull thread in the first direction. As a result, a part of the loop is withdrawn into the lumen in the insertion portion, the length of the loop disposed on the outer side of the distal end of the insertion portion is reduced, and thus, the object inside the loop can be temporarily tightened.

At this stage, when the temporary tightening state is not satisfactory, the first state is switched to the second state so as to pull the ligature and let out the pull thread simultaneously in the second direction opposite to the first direction. As a result, pulling of the pull thread is relaxed, and the ligature, which has been withdrawn into the lumen, is pulled out of the lumen to increase the length of the loop so that the temporary tightening can be re-adjusted. When the temporary tightening state is satisfactory, while maintaining the temporary tightening state, the second end of the ligature and the second end of the pull thread are anchored to the movable member, and the movable member is moved. As a result, the ligature is pulled, and the pull thread is let out.

When the ligature is pulled, the loop is contracted. Meanwhile, since the pull thread is let out, the part of the loop withdrawn into the lumen is pulled out of the lumen. Since the ligature and the pull thread are pulled or let out by the movement of the same movable member, the state of temporary tightening of the object by the ligature can smoothly be transitioned to the full tightening state by the ligature. In other words, according to this aspect, temporary tightening and full tightening can be performed by using a ligature loop without using a snare.

In the aspect described above, in the first state, the ligature may be attached to the operation portion and the second end of the pull thread may be pulled, and in the second state, the ligature may be attached to the movable member, and the ligature is pulled and the pull thread may be let out simultaneously.

In the aspect described above, the ligation device may also include a first attaching portion to which a second end of the ligature is to be attached, the first attaching portion provided in the operation portion; and a second attaching portion to which the second end of the ligature extending to the outside from a proximal end of the lumen is to be attached, the second attaching portion provided in the movable member. When the movable member is in the first state, the second end of the ligature may be attached to the first attaching portion, and in the second state, the second end of the ligature may be attached to the second attaching portion.

In the aspect described above, the movable member may switched between the first state in which the second end of the pull thread is pulled by a predetermined length, and a second state in which the ligature is pulled and the pull thread is let out by the predetermined length simultaneously.

In the aspect described above, when the movable member is in the first state, the movable member may be moved relative to the operation portion so that the pull thread is pulled, and the second end of the ligature may be detachably anchored to the movable member at a position where a part of the loop is withdrawn into the lumen.

In the aspect described above, when the movable member is in the first state, the pull thread may be pulled, and the second end of the ligature may be detachably anchored to the movable member at a position where the folded-back portion of the pull thread is withdrawn by a length equal to one half of the predetermined length.

In the aspect described above, the ligation device may further include a pulley that is provided in the operation portion and folds back the ligature, and the movable member may be a slider linearly movable in the longitudinal direction of the pull thread, and the ligature folded back by the pulley may be to be detached from or attached to the slider.

In this manner, the second end of the pull thread pulled out of the lumen in the insertion portion so as to be on the proximal end side is anchored to the movable member, and the second end of the ligature is folded back by the pulley and anchored to the same movable member. In this state, when the movable member is linearly moved in the longitudinal direction of the pull thread, the ligature is pulled and the pull thread is let out simultaneously. As a result, the object to be tightened can be easily switched to the full tightening state while maintaining the temporary tightening state of the object by the loop.

In the aspect described above, the movable member may be a spool member rotatable about an axial line extending in a direction orthogonal to the longitudinal direction of the pull thread, and the second end of the ligature may be attached to the movable member so that a winding direction of the ligature is opposite to a winding direction of the pull thread.

In this manner, the second end of the pull thread pulled out of the lumen in the insertion portion so as to be on the proximal end side is anchored to the movable member, which is a spool member, by being wound in one direction, and the second end of the ligature is anchored to the same movable member by being wound in the other direction. In this state, when the movable member is rotated in the other direction, the ligature is pulled and the pull thread is let out simultaneously. As a result, the object to be tightened can be easily switched to the full tightening state while maintaining the temporary tightening state of the object by the loop.

In the aspect described above, when the movable member is in the first state, the ligature may be pulled in a proximal end direction, and the second end of the pull thread in a state in which a part of the loop is withdrawn into the lumen may be detachably anchored to the movable member.

In this manner, when the movable member is moved in the first direction to pull the pull thread and temporarily tighten the object, and when the second end of the ligature is attached to the movable member and the movable member is moved in the opposite direction, the object can be fully tightened.

In the aspect described above, the ligature may be pulled in the proximal end direction, and the second end of the pull thread in a state in which the folded-back portion of the pull thread may be withdrawn by one half of the predetermined length is detachably anchored to the movable member.

In this manner, when the second end of the pull thread is attached to the movable member and the movable member is moved while the object is temporarily tightened by pulling the pull thread, the ligature is pulled and the pull thread is let out by the same amount of movement, and thus the object can be easily fully tightened.

In the aspect described above, the ligation device may further include a pulley that folds back the pull thread, the pulley being provided in the operation portion, the movable member may be a slider linearly movable in the longitudinal direction of the ligature, and the pull thread folded back by the pulley may be detachably attached to the slider.

In this manner, the second end of the ligature pulled out of the lumen in the insertion portion so as to be on the proximal end side is anchored to the movable member, and the second end of the pull thread pulled to temporarily tighten the object is folded back by the pulley and anchored to the same movable member. In this state, when the movable member is linearly moved in the longitudinal direction of the pull thread, the ligature is pulled and the pull thread is let out simultaneously. As a result, the object to be tightened can be easily switched to the full tightening state while maintaining the temporary tightening state of the object by the loop.

In the aspect described above, the movable member may be a spool member rotatable about an axial line extending in a direction orthogonal to the longitudinal direction of the ligature, and the second end of the pull thread may be attached to the movable member so that a winding direction of the pull thread is opposite to a winding direction of the ligature.

In this manner, the second end of the ligature pulled out of the lumen in the insertion portion so as to be on the proximal end side is anchored to the movable member, which is a spool member, by being wound in one direction, and the second end of the pull thread pulled to temporarily tighten the object is anchored to the same movable member by being wound in the other direction. In this state, when the movable member is rotated in the one direction, the ligature is pulled and the pull thread is let out simultaneously. As a result, the object to be tightened can be easily switched to the full tightening state while maintaining the temporary tightening state of the object by the loop.

In the aspect described above, the insertion portion may have a plurality of the lumens, and the ligature and the pull thread may be disposed in different lumens.

In this manner, the ligature and the pull thread can be smoothly pulled and let out without interference.

In the aspect described above, the insertion portion may have one lumen, and a knot receiving portion that has a penetrating hole having a diameter larger than a line diameter of the ligature and smaller than the knot may be installed at a distal end of the insertion portion.

In this manner, only one lumen is provided and the diameter of the insertion portion can be reduced. When the ligature is pulled, the knot is caught on the knot receiving portion and retained on the outer side of the distal end of the insertion portion, and thus the loop can be easily contracted.

In the aspect described above, when the movable member is in the first state, the second end may be pulled in a first direction, and in the second state, the ligature is pulled and the pull thread may be let out simultaneously in a second direction opposite to the first direction.

REFERENCE SIGNS LIST 1 ligation device
2, 3, 13 lumen
4 insertion portion
5 operation portion
6 ligature
6a loop
6b knot
7 pull thread
8a anchoring portion
8b attaching portion (first attaching portion)
9 slider (movable member)
10 pulley
11 attaching portion (second attaching portion)
12 spool member (movable member)
14 knot receiving portion

The invention claimed is:

1. A ligation device comprising:
an insertion portion that has a lumen through which are passed a ligature having a first end having a contractible loop formed by a knot, and a pull thread having a folded-back portion fed through the loop;
an operation portion disposed on a proximal-end side of the insertion portion, the operation portion including an anchoring portion to which a first end of the pull thread is anchored;
a movable member movable relative to the operation portion while switching between a first state in which a second end of the pull thread is anchored to the movable member and pulled and a second state in which the ligature is pulled and the pull thread is let out simultaneously; and
a pulley that is provided in the operation portion and folds back the ligature;
wherein, when the movable member is in the first state, the movable member is moved relative to the operation portion so that the pull thread is pulled, and a second end of the ligature is detachably anchored to the movable member at a position where a part of the loop is withdrawn into the lumen; and
the movable member is a slider linearly movable in a longitudinal direction of the pull thread, and the ligature folded back by the pulley is to be detached from or attached to the slider.

2. The ligation device according to claim 1, wherein the insertion portion has a plurality of the lumens, and
the ligature and the pull thread are disposed in different lumens.

3. The ligation device according to claim 1, wherein, in the first state, the ligature is attached to the operation portion and the second end of the pull thread is pulled, and
in the second state, the ligature is attached to the movable member.

4. The ligation device according to claim 3, further comprising:
- a first attaching portion to which the second end of the ligature is to be attached, the first attaching portion provided in the operation portion; and
- a second attaching portion to which the second end of the ligature extending to the outside from a proximal end of the lumen is to be attached, the second attaching portion provided in the movable member,
- wherein when the movable member is in the first state, the second end of the ligature is attached to the first attaching portion, and in the second state, the second end of the ligature is attached to the second attaching portion.

5. The ligation device according to claim 1, wherein the movable member switches between the first state in which the second end of the pull thread is pulled by a predetermined length, and the second state in which the ligature is pulled and the pull thread is let out by the predetermined length simultaneously.

6. The ligation device according to claim 5, wherein, when the movable member is in the first state, the pull thread is pulled, and the second end of the ligature is detachably anchored to the movable member at a position where the folded-back portion of the pull thread is withdrawn by a length equal to one half of the predetermined length.

* * * * *